United States Patent

Liang et al.

[11] Patent Number: 5,859,019
[45] Date of Patent: Jan. 12, 1999

[54] METHODS FOR PROTECTING AGAINST CARDIAC ISCHEMIA BY ADMINISTERING ADENOSINE $A_{2A}$ RECEPTOR ANTAGONISTS

[75] Inventors: Bruce T. Liang, Merion Station, Pa.; Kenneth A. Jacobson, Silver Spring, Md.

[73] Assignees: Trustees of the University of Pennsylvania, Philadelphia, Pa.; National Institute of Health, Rockville, Md.

[21] Appl. No.: 813,787

[22] Filed: Mar. 7, 1997

[51] Int. Cl.$^6$ .................. A61K 31/505; A61K 31/52; A61K 31/53
[52] U.S. Cl. .................. 514/263; 514/245; 514/267
[58] Field of Search ................. 514/262, 245, 514/267, 263

[56] References Cited

U.S. PATENT DOCUMENTS

| | | | |
|---|---|---|---|
| 5,443,386 | 8/1995 | Downey et al. | 424/423 |
| 5,573,772 | 11/1996 | Downey et al. | 424/423 |

OTHER PUBLICATIONS

Liang et al. (1996) J. Biol. Chem. 271:18678–18685.
Kim et al. (1994) J. Med. Chem. 37:3614–3621.
Jacobson et al. (1993) J. Med. Chem. 36:1333–1342.
Jacobson et al. (1993) FEBS 323:141–144.
Gallo–Rodriquez et al. (1994) J. Med. Chem. 37:636–646.
Babbitt et al. (1988) Circulation 80:1388–1399.
Olafsson et al. (1987) Laboratory Investigation:Reperfusion 76:1135–1145.
Auchampach et al. (1992) Cardiovascular Research 26:1054–1062.
Miura et al. (1992) Circulation 86:979–985.
Li et al. (1990) Circulation 82:609–619.
Ikonomidis (1994) Cardiovascular Research 28:1285–1291.
Webster et al. (1995) Mol. Cell. Cardiol. 27:453–458.
Liu et al. (1994) Cardiovascular Research 28:1057–1061.
Armstrong et al. (1994) Cardiovascular Research 28:1049–1056.
Deutsch et al. (1990) Circulation 82:2044–2051.
Tomai et al. (1994) Circulation 90:700–705.
Van Wylen et al. (1994) Circulation 89:2283–2289.
Schulz et al. (1994) American J. Physiology 267 Heart Circ. Physiol. 36: H1341–H1352.
Yamane et al. (1991) J. of Immunoassay 12:501–519.
Downey (1992) Trends in Cadiovasc. Med. 2:170–176.
Yao et al. (1993) Circulation 89:1229–1236.
Ely et al. (199) Circulation 85: 893–904.
Mestril et al. (1993) J. Clin. Invest. 93:759–767.
Liang et al. (1995) Circ. Res. 76:242–251.
Liang (1992) Trends in Cardiovascular Med. 2:100–108.
Phillis, J. W., Brain Res. 705 (1,2) 79–84 (1995.
Huang et al., Am. J. Physiol. 269/2 38–2 (R318–R–324) 1995.

*Primary Examiner*—Phyllis G. Spivack
*Attorney, Agent, or Firm*—Dann, Dorfman, Herrell and Skillman

[57] ABSTRACT

Methods for reducing or preventing ischemic damage of the heart are disclosed. A preferred embodiment of the invention comprises the administration of a specific $A_{2a}$ receptor antagonist, 8-(3-chlorostyryl) caffeine, to patients suffering from ischemic damage or at risk for the same.

20 Claims, 4 Drawing Sheets

METHODS FOR PROTECTING AGAINST CARDIAC ISCHEMIA BY ADMINISTERING ADENOSINE $A_{2A}$ RECEPTOR ANTAGONISTS Pursuant to 35 U.S.C. §202(c) it is acknowledged that the U.S. Government has certain rights in the invention described herein, which was made in part with funds from the National Institutes of Health, Grant Number HL48225.

FIELD OF THE INVENTION

The present invention relates to methods of administrating compounds to protect the heart from ischemic injury. More specifically, the invention provides antagonists which selectively inhibit activation of $A_{2a}$ receptors thereby enhancing the protective effects of preconditioning and rendering the heart more resistant to ischemia.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

Preconditioning (PC) with brief ischemia before a sustained period of ischemia has been shown to reduce infarct size in isolated perfused heart. This preconditioning phenomenon has been observed in perfused hearts from a number of mammalian species including dog, guinea pig, pig, rabbit, and rat (1–6, 10–13). Indirect evidence for protective preconditioning also exists in humans (5, 6, 14). Adenosine is released in large amounts during myocardial ischemia and has been demonstrated to play a major role in mediating preconditioning and other cardioprotective effects in most animal species including humans (1–14). Previous studies (15–17) of adult human and rabbit ventricular myocytes and cultured neonatal rat cardiac myocytes provided important insight by indicating that the cardioprotective mechanism of preconditioning is exerted, at least in part, at the level of and by the cardiac myocytes in the intact heart. Although a non-$A_1$ receptor, possibly the $A_3$ subtype, may be involved in mediating preconditioning, very little is known regarding the role of different adenosine receptor subtypes in mediating or modulating preconditioning of the cardiac myocytes.

Ventricular myocytes cultured from chick embryos retain many of the properties of the intact heart and have served as a useful model for a variety of experimental paradigms (18–24). Previous studies have demonstrated that activation of adenosine receptors in these cultured heart cells produces physiologic effects similar to those elicited by adenosine in the adult mammalian heart (25–28). The cultured ventricular myocytes contain predominantly (>90%) myocytes (21) and are largely devoid of neuronal, blood or vascular cells, thus the confounding influence of changes in blood flow is avoided (18–28). This chick ventricular cell culture provides a model system to investigate the role of adenosine receptor subtypes in the preconditioning process and to study the mechanism(s) by which preconditioning of the ventricular myocytes can be modulated. To simulate preconditioning, ventricular myocytes were exposed to five minutes of hypoxia ($O_2 < 1\%$), reoxygenated in the presence of normal % $O_2$ (room air) for ten minutes, and then incubated in the presence of continuous hypoxia for ninety minutes ($O_2 < 1\%$). The development of a ventricular myocyte model for preconditioning and the use of a protocol identical to that employed in preconditioning of the isolated perfused heart facilitates cellular characterization of this phenomenon and enables quantitative determination of the extent of cardioprotection by preconditioning.

Use of this model has facilitated the identification of compounds that enhance the protective effects of preconditioning and that increase myocardial resistance to ischemia.

SUMMARY OF THE INVENTION

The present invention provides methods for preventing ischemic damage of the heart. In conducting research leading up to invention, it was discovered that activation of $A_{2a}$ receptors inhibits the protective effects of preconditioning and decreases myocardial resistance to ischemia. The inventive concept underlying the present invention is the use of specific $A_{2a}$ antagonists to counteract the inhibitory effects of $A_{2a}$ receptor activation during an ischemic attack.

According to a preferred embodiment, the invention involves administration of a specific $A_{2a}$ antagonist, 8-(3-chlorostyryl) caffeine (CSC) to patients during ischemic attacks, or at risk for ischemic damage. The antagonists of the invention may be delivered prior to a surgical procedure. They may also be administered to a patient to prevent or reduce the severity of ischemic damage during surgery. Additionally, the $A_{2a}$ antagonists may be administered following surgical procedures to reduce the risk of post-surgical ischemic complications. Finally, the $A_{2a}$ antagonists may be administered to patients with angina. The angina may be chronic and stable, unstable or due to post-myocardial infarction.

Methods of administration of the $A_{2a}$ antagonists of the invention include direct perfusion of the organ during surgery and intravenous administration. Additionally, the antagonists of the invention may be administered to patients in tablet form in an amount effective to prevent or reduce ischemic damage of the heart.

DETAILED DESCRIPTION OF THE INVENTION

Figure 1:
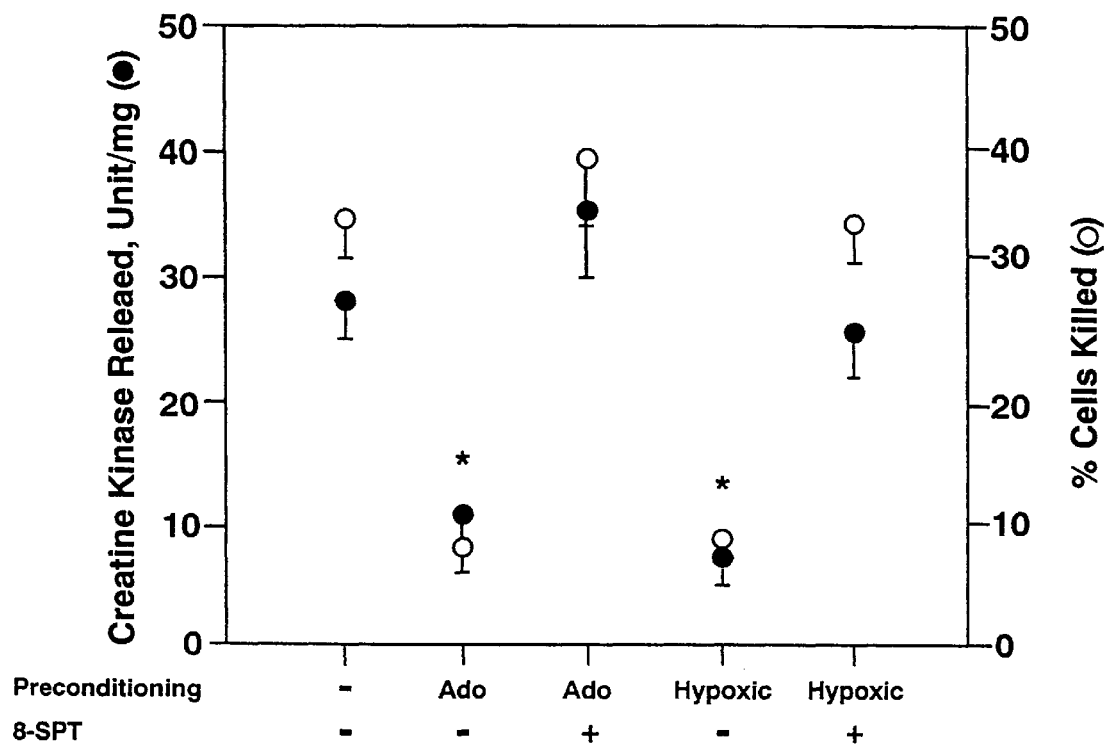
FIG. 1 is a graph illustrating the effects of preconditioning of ventricular cells using adenosine and hypoxia. Data are presented as percent cells killed (○) or as amount of creatine kinase (CK) released (●) and represent the mean ±SE of six to eight experiments.

Preconditioning with brief ischemia before a sustained period of ischemia reduces infarct size in the perfused heart. A cultured chick ventricular myocyte model was developed to investigate the role of certain adenosine receptor subtypes in cardiac preconditioning. Brief hypoxic exposure, termed preconditioning hypoxia, prior to prolonged hypoxia, protected myocytes against injury induced by the prolonged hypoxia. Activation of the adenosine $A_1$ receptor with CCPA or the $A_3$ receptor with C1-IB-MECA can replace preconditioning hypoxia and simulate preconditioning, with a maximal effect at 100 nM. While activation of the $A_{2a}$ receptor by 1 μM CGS21680, a specific $A_{2a}$ agonist, could not mimic preconditioning, its stimulation during preconditioning hypoxia attenuated the protection against hypoxia-induced injury. In accordance with the present invention, it has been discovered that blockade of $A_{2a}$ receptors with a selective antagonist, e.g., CSC (1 μM) during preconditioning hypoxia enhanced the protective effect of preconditioning. Nifedipine, which blocked the $A_{2a}$ receptor-mediated calcium entry, overcame the $A_{2a}$ agonist-induced attenuation of preconditioning. Isoproterenol, forskolin, and BayK 8644, which stimulated calcium entry, also attenuated preconditioning. Nifedipine blocked the increase in calcium uptake by these agents as well as their attenuating effect on preconditioning. The data demonstrate, for the first time, that activation of the $A_{2a}$ receptor antagonizes the preconditioning effect of adenosine, with increased calcium entry during the preconditioning stimuli as a novel mechanism. This observation provides a novel approach for enhancing the protective effects of preconditioning on heart muscle via the administration of specific $A_{2a}$-receptor antagonists to patients suffering from, or at risk for ischemic damage of the heart.

The following definitions are provided to facilitate understanding of the present invention.

Preconditioning ischemia—A brief ischemia which does not cause any cardiac damage, but is able to protect the heart against damage during a subsequent prolonged ischemia. The effect of preconditioning ischemia is mediated by adenosine, which is released during the ischemia.

Adenosine receptors—$A_1$, $A_3$ and $A_{2a}$ receptors are present on the myocardium (cardiac muscle cells). While activation of the $A_1$, and $A_3$ receptors is cardioprotective, activation of the $A_{2a}$ receptors is deleterious and causes damage to the cardiac muscle cells.

Stable angina—Certain patients have a chronic risk for myocardial ischemia because of the chronic potential for an imbalance between the supply of oxygenated blood and the demand for it. Typically, such imbalance occurs during certain stresses, such as exercise, emotional stress or stress associated with a surgical procedure.

Unstable angina—Patients have frequent imbalance between the supply of and the demand for oxygenated blood.

Post-myocardial infarction angina—This condition is observed in patients who have recurrent ischemia following a heart attack.

Preconditioning stimuli—Any drug, agent or treatment which induces preconditioning, such as brief ischemia, or $A_1$ or $A_3$ receptor agonists.

Myocardial responsiveness—The myocardium can be treated so as to enhance the effectiveness and protective effects of preconditioning. This enhancement leads to a reduction in ischemic damage.

Preparation and Preconditioning of Cultured Ventricular Cells

Ventricular cells were cultured from chick embryos 14 days in ovo, according to a previously described procedure (20, 27). Cells were plated at a density of 400,000 cells per ml and cultivated in a humidified 5% $CO_2$-95% air mixture at 37° C. All experiments were performed on day 3 in culture, at which time cells grew to confluence and exhibited rhythmic spontaneous contraction. For preconditioning studies, the medium was changed to a HEPES-buffered medium containing (mM) 139 NaCl, 4.7 KCl, 0.5 $MgCl_2$, 0.9 $CaCl_2$, 5 HEPES (N-2-hydroxyethylpiperazine-N'-2-ethanesulfonic acid) and 2% fetal bovine serum, pH=7.4, 37° C. before exposing cells to the various conditions at 37° C. Control cells were maintained in the HEPES-buffered media under room air. Hypoxia was produced by placing the cells in a hypoxic incubator (NuAire) where $O_2$ was replaced by $N_2$. The % $O_2$ was monitored by both an oxygen Fyrite Gas Analyzer (Bacharach) and an oxygen analyzer (Model OX630, Engineered Systems & Designs). Preconditioning was induced by exposing the cells to five minutes of hypoxia, termed preconditioning hypoxia, prior to a second ninety-minute hypoxia. Cells not subjected to preconditioning were exposed to ninety minutes of hypoxia only (nonpreconditioned cells). The extracellular pH was similarly maintained at 7.4 by HEPES in both preconditioned and nonpreconditioned cells. Determination of basal level of cell injury was made after parallel incubation of control cells under normal % $O_2$. For preconditioned and nonpreconditioned cells, determination of cell injury was made at the end of the ninety-minute hypoxic period.

Measurement of $^{45}Ca$ Uptake and Cyclic AMP Level

Determination of $^{45}Ca$ uptake was made according to a modification of previously described method (20). Cultures were incubated with L-(3, 4, 5-$^3H$, N)-leucine (152.2 Ci/mmol) for a 24 hour prior to $^{45}Ca$ uptake. [$^3H$] leucine incorporated into the cellular protein allowed normalization of $^{45}Ca$ content to mg cell protein. After incubation with $^{45}Ca$-containing medium, cells were then washed free of $^{45}Ca$ and solubilized for 2 hours with 1% sodium dodecyl sulfate and 10 mM sodium borate and the levels of $^3H$ and $^{45}Ca$ were determined. For all data comparing the effect of different agents on $^{45}Ca$ uptake, one-way ANOVA analysis followed by group comparison with t-test was carried out at each time point of the $^{45}Ca$ uptake. Cyclic AMP level was determined according to a previously described radioimmunoassay (27).

Determination of Cell Injury

The extent of hypoxia-induced injury to the ventricular cell was quantitatively determined by the percentages of cells killed and by the amount of creatine kinase (CK) released into the media. To quantitate the % cells killed, cells were exposed to a trypsin-EDTA Hanks' balanced salt solution for 10 minutes for detachment after the various treatment, followed by centrifugation (300 × g for 10 minutes) and resuspension in culture media for counting in a hemocytometer. Only live cells sedimented and the cells counted represented those that survived (29). None of the sedimented cells subsequently counted included trypan blue. In cells not exposed to hypoxia, trypsin-EDTA treatment followed by re-exposure to $Ca^{2+}$-containing culture media did not cause the appearance of trypan blue-stained cells or any significant increase in proteins or CK in the trypsin-EDTA media following the 300 × g, 10 minute sedimentation of the cells. There was no protein or CK in the culture media following a second 300 × g centrifugation of resuspended cells previously treated with trypsin-EDTA. Thus, trypsin treatment, re-exposure to $Ca^{2+}$-containing media or 300 × g sedimentation did not cause any significant damage to the control, normoxia-exposed cells. In contrast, the trypsin-EDTA media from cells exposed to 90 minutes of hypoxia contained substantial amount of proteins (0.15±0.03 mg, n=9) and CK activity (16±3 unit/mg protein, n=8). Such proteins and CK activity could arise from hypoxia-damaged cells which failed to sediment because of lighter cellular density from loss of soluble proteins or from hypoxia-exposed cells that were further damaged by the trypsin treatment. Because trypsin may cause further proteolysis of proteins and CK, the amount of protein and CK retained by the damaged cells in the trypsin-EDTA media may not accurately reflect those associated with the damaged cells. In support of the notion that exposure to 90 minutes of hypoxia caused significant cell injury and loss of membrane integrity, there was also marked release of LDH (hypoxia-exposed cells, 35.5±2.7, unit/mg, n=8, ±S.E. vs. control cells, 6.1±0.4 unit/mg, n=8) and proteins (hypoxia-exposed cells, 0.15±0.03 mg, n=8 vs. control cells, 0.034±0.01 mg, n=8) from the cells incubated under prolonged hypoxia. Thus, the cell viability assay separated out the hypoxia-damaged from the control normoxia-exposed cells. Parallel changes in % cells killed and CK released as illustrated in FIG. 1, further validated this assay for assessing the percentage of cells killed. The amount of CK was measured as enzyme activity (unit/mg), and increases in CK activity above the control level were determined. The percentage of cells killed was calculated as the number of cells obtained from the control group (representing cells not subjected to any hypoxia or drug treatment) minus the number of cells from the treatment group divided by number of cells in control group multiplied by 100%.

Adenosine Measurement and Synthesis of Adenosine Receptor Selective Agonists

Adenosine concentrations in the buffer media were measured by an adenosine radioimmunoassay using antiserum specific to adenosine, which does not cross react with inosine or adenine nucleotides (30, 31). The recovery of adenosine standard, when added to the media containing the endogenous adenosine, was 96.4±7.2%, n=8, ±S.E. The electrolytes $Na^+$, $K^+$, and $Cl^-$ were determined by ion-selective electrodes in a Boehringer Mannheim/Hitachi 747 analyzer using reagents supplied by Boehringer Mannheim (32). 8-(3-chlorostyryl)caffeine (CSC), $N^6$-(3-iodobenzyl)adenosine-5'-N-methyluronamide (IB-MECA) and 2-chloro-$N^6$-(3-iodobenzyl)adenosine-5'-N-methyluronamide (Cl-IB-MECA) were synthesized as described (33–35).

The following examples are provided to illustrate certain embodiments of the invention. They are not intended to limit the invention in any way.

EXAMPLE I

Hypoxic Preconditioning of Cultured Ventricular Cells

Cultured ventricular cells were preconditioned by a five-minute preconditioning hypoxia prior to a ninety-minute period of sustained hypoxia. The concentration of Na+ (140 mM), K+ (4.5 mM), Cl– (145 mM), and the pH (7.44) of the buffer media did not change in control, preconditioned or nonpreconditioned cells. The level of adenosine in culture media was subsequently determined. In preconditioned cells, both five-minute and ninety-minute hypoxia produced significant increases in adenosine in the media (Basal adenosine level: 21±2 nM, ±SE of triplicates; After 5-min hypoxia: 32±2.6 nM; After 90-min hypoxia: 70±5.5 nM; data were typical of 9 experiments; ANOVA and paired t test p<0.01) However, the extent of increase in adenosine produced by the ninety-minute hypoxia in preconditioned cells was less than that of the increase in nonpreconditioned cells (310±46%, n=10, ±S.E. vs. 468±33%, n=10; P<0.01, t test), similar to the finding in preconditioning of the isolated perfused heart (36).

Five minutes of hypoxic exposure did not result in a significant increase in CK release or in any cell death (not shown). Ninety minutes of hypoxic exposure resulted in a significant proportion of cells killed and a large increase in the release of CK into the media. Preconditioning hypoxia caused pronounced reductions in the percentage of cells killed (70.4±4%) and in the CK released (69±3%) See FIG. 1. There was minimal variability of proteins from one culture plate to another within the same culture (a typical culture has 0.9±0.03 mg protein per 60 mm dish, ±S.D., n=20 dishes). For all experiments, data on CK activity was normalized to total amount of protein content per 60 mm dish determined for each culture. The duration of the preconditioning effect was between thirty and sixty minutes, such that protection against cell injury was still evident thirty minutes after the preconditioning hypoxia but was lost at sixty minutes (data not shown).

Role of Adenosine Receptors in Mediating Preconditioning

To investigate the role of adenosine in mediating the preconditioning effect, the ventricular cells, instead of being exposed to the brief hypoxia, were incubated with adenosine (10 μM) for 5 minutes prior to the ninety minute hypoxia. In adenosine-treated cells, media were replaced with adenosine-free media for ten minutes prior to a ninety-minute hypoxic exposure. Effects of a non-selective adenosine receptor antagonist 8-sulfophenyltheophylline (8-SPT, 100 μM) on adenosine- or hypoxia-induced preconditioning, where 8-SPT was added during the five-minute exposure to adenosine or hypoxia, were also determined. The nonpreconditioned cells were exposed to ninety minutes of hypoxia only. Data are presented as % cells killed (○) or as amount of creatine kinase (CK) released (●) and were mean ±SE of six to eight experiments. The asterisk (*) indicates that the difference from nonpreconditioned cells or from cells preconditioned in the presence of 8-SPT was statistically significant (one-way ANOVA analysis using F value, followed by group comparison employing unpaired t test where p<0.01).

Adenosine did not cause any cell injury but elicited a significant attenuation of the injury produced by the subsequent ninety-minute hypoxia (P<0.01 compared to nonpreconditioned cells, t test). See FIG. 1. The non-selective adenosine receptor antagonist 8-sulfophenyltheophylline (8-SPT, 100 μM), when added during the 5 minute exposure to adenosine or preconditioning hypoxia, completely abolished the preconditioning effect induced by adenosine or the preconditioning hypoxia, respectively as shown in FIG. 1. These data indicate that adenosine receptor activation initiated the preconditioning. Continued activation of the adenosine receptor was required to sustain preconditioning because the presence of 8-SPT during the ninety-minute hypoxia was also able to completely abolish its protective effect. Such role of adenosine receptor is similar to that of the receptor in preconditioning of the intact heart (2, 3).

Adenosine $A_{2a}$ Receptor Activation Attenuates Preconditioning

Figure 2:
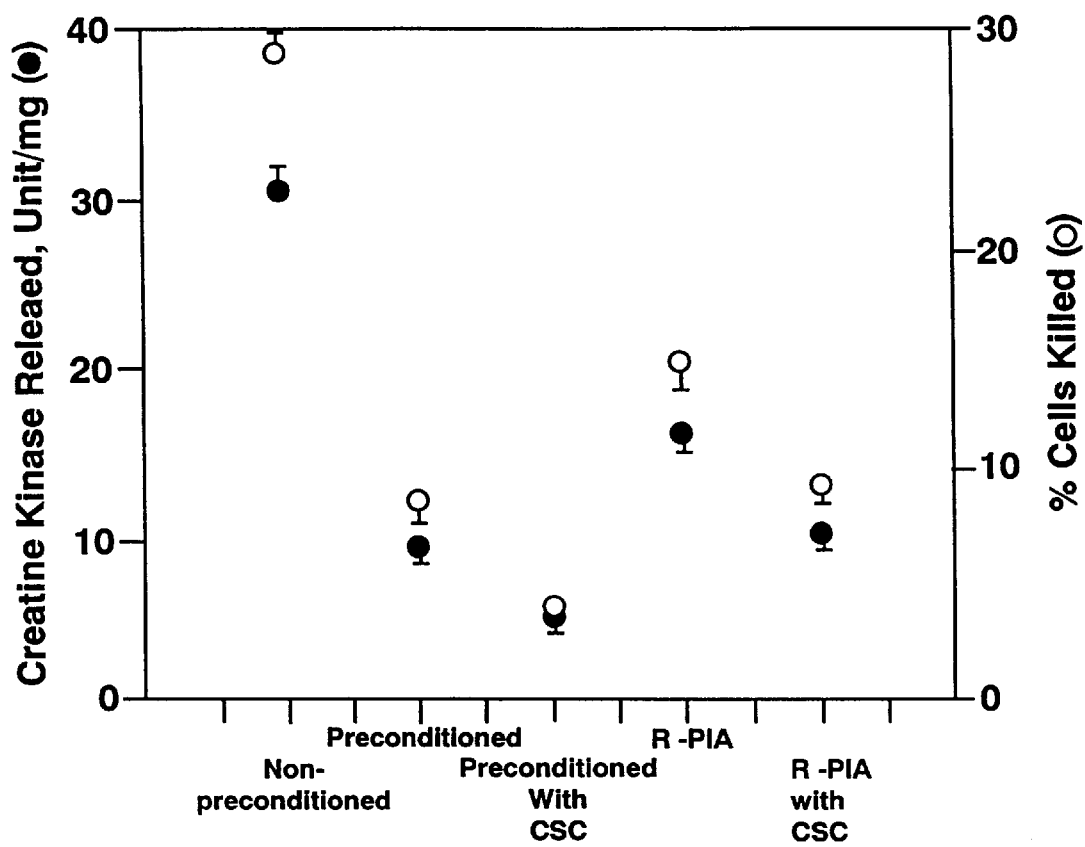
FIG. 2 is a graph illustrating the effect of adenosine $A_{2a}$ receptor activation on the protective effect of preconditioning hypoxia. Data were plotted as % cells killed (○) or as amount of CK released (●). Data were the mean and standard errors of five experiments from five separate cultures.

The adenosine receptor agonist R-PIA could substitute for preconditioning hypoxia and induce preconditioning, but the $A_{2a}$ receptor-selective agonist CGS21680 could not (not shown). Compared to preconditioned cells, blocking of the adenosine A2a receptor with its selective antagonist 8-(chlorostyryl)caffeine (CSC) (27, 33) during preconditioning hypoxia resulted in increased protection as can be seen in FIG. 2. Ventricular cells were preconditioned by a five-minute exposure to hypoxia in the presence or absence of the $A_{2a}$ receptor-selective antagonist CSC (1 $\mu$M). Media, with or without the adenosine compounds, were obtained after the preconditioning hypoxia for CK measurement and were replaced with fresh media prior to ninety-minute hypoxia. The effect of CSC on $N^6$-R-phenyl-2-propyl adenosine (R-PIA)-induced preconditioning was also tested. Cells preconditioned by the five-minute treatment with 10 $\mu$M R-PIA in the presence or the absence of CSC were exposed to the ninety-minute hypoxia after R-PIA was removed by replacement with fresh media. The data were plotted as the percentage of cells killed (open circles) or as the amount of CK released (closed circles). CSC enhanced the preconditioning effect induced by 10 $\mu$M R-PIA, which could activate not only the $A_1$ or $A_3$ receptors but also the $A_{2a}$ receptor, with a further decrease in % cells killed and in the amount of CK released compared to cells preconditioned by R-PIA alone (FIG. 2) (P<0.01, t test). Prior exposure of the ventricular cells to CSC in the absence of preconditioning hypoxia had no effect on the extent of injury induced by the ninety-minute hypoxia (not shown). Such data further supported the notion that $A_{2a}$ receptor activation can attenuate preconditioning. See FIG. 2.

In contrast, activation of the $A_{2a}$ receptor by its agonist CGS21680 during preconditioning hypoxia attenuated the protection and an increase in the % cells killed and in the amount of CK released (ANOVA and t test, P<0.01) was observed.

Mechanism Underlying the $A_{2a}$ Receptor-Mediated Attenuation of Preconditioning Activation of the adenosine $A_{2a}$ receptor by CGS21680 (1 $\mu$M) led to nifedipine-sensitive increase in calcium entry. The levels of $^{45}$Ca uptake after 90-second exposure to $^{45}$Ca-containing media, in nmol/mg, were 4.2±0.1 for control, 5.8±0.2 for CGS21680 stimulated, and 4.4±0.1 for CGS21680 plus nifedipine (1 $\mu$M) stimulated cells (±S.D., representative of five experiments). Thus, an increase in calcium entry during hypoxia- or R-PIA-induced preconditioning may be the mechanism by which $A_{2a}$ receptor activation attenuated the protection conferred by preconditioning. This notion was supported by the finding that nifedipine (1 $\mu$M) abolished the CGS21680-induced attenuation of cardioprotection induced by preconditioning hypoxia (P>0.1 compared to cells preconditioned in the absence of CGS21680 or nifedipine, t test).

To test the hypothesis, the effect of isoproterenol (0.3 $\mu$M), forskolin (1 $\mu$M) and BayK 8644 (0.1 $\mu$M) on the preconditioning responsiveness was determined.

Figure 3A:
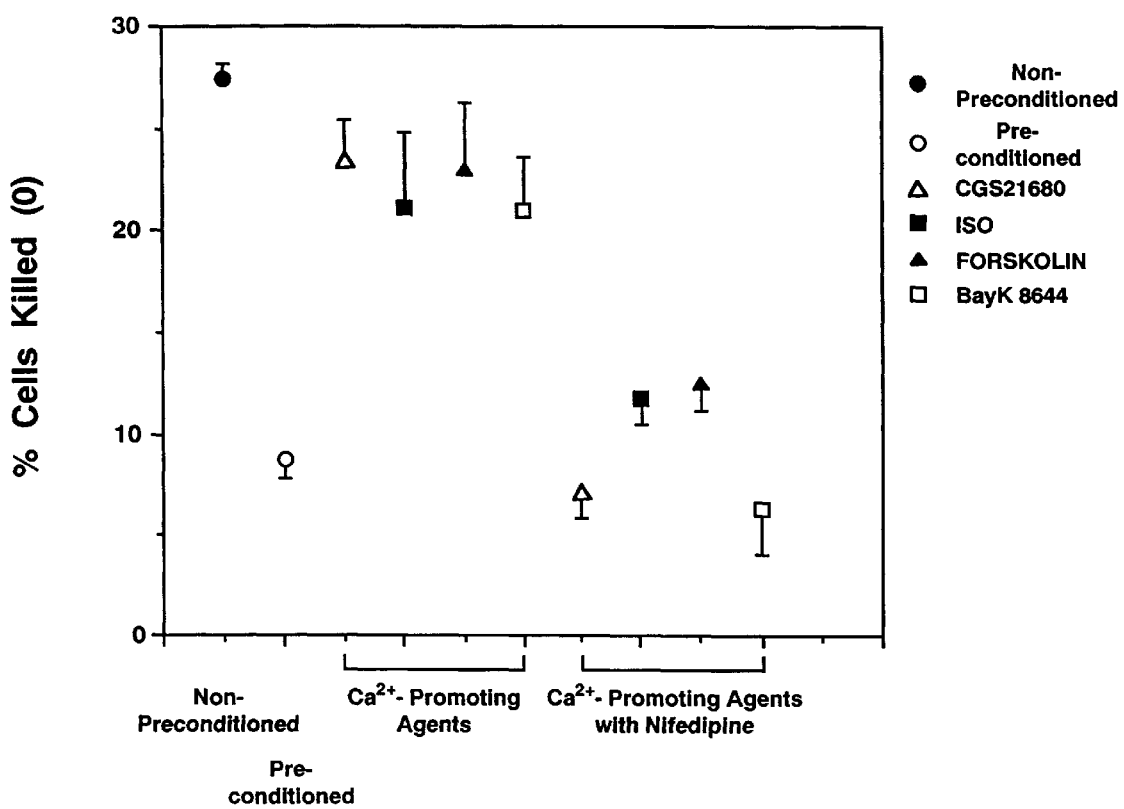
FIG. 3 is a graph illustrating the effects of nifedipine which blocked the ability of 2-[4-(2-carboxyethyl) phenylethylamino]-5'-N-ethylcarboxiamidoadenosine (CGS21680), isoproterenol, forskolin and BayK 8644 to attenuate preconditioning. Data were plotted as % cells killed (A) or as the amount of CK released (B) and were the mean and standard error of five experiments from five cultures. (● Non-preconditioned; ○ pre-conditioned; ΔCG521680; ■ ISO; ▲ Forskolin; □ BayK 8644.)
Figure 3B:
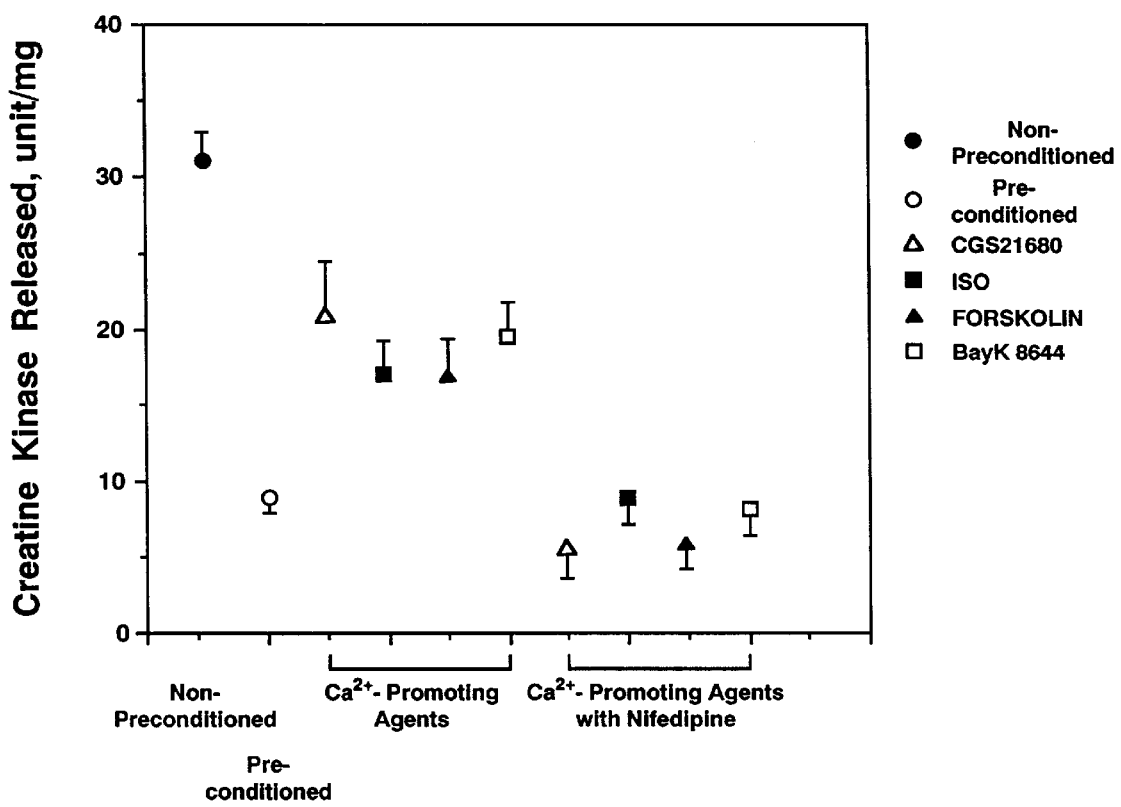

Ventricular cells were preconditioned by a five-minute exposure to hypoxia in the presence or absence of the various agents indicated. After replacing with fresh media, the preconditioned cells were exposed to ninety minutes of hypoxia as were the nonpreconditioned cells. See FIG. 3. All three agents induced increased calcium influx into the cultured cells (not shown). Both isoproterenol and forskolin stimulated calcium influx by increasing cyclic AMP accumulation (% increase in cAMP level by isoproterenol: 228±31%, n=6, ±S.E. vs. by forskolin: 54.8±9.7%, n=6) while BayK 8644 activated the calcium channel directly. All three agents, when present during preconditioning hypoxia, caused an increase in % cells killed and amount of CK released (P<0.01 compared to cells preconditioned in the absence of any agent, ANOVA and t test). See FIG. 3. The deleterious effect of all three agents on the preconditioning response was abolished by 1 $\mu$M nifedipine (P>0.1 compared to cells preconditioned in the absence of added agent), indicating that increased calcium entry during preconditioning hypoxia is the mechanism mediating the decreased responsiveness to preconditioning. Neither the calcium entry-promoting agents nor nifedipine had any effect on the extent of injury caused by the ninety-minute hypoxia when these agents were present only during the preconditioning episode and not during the subsequent ninety-minute hypoxia (not shown).

EXAMPLE II

The preconditioning effect described herein has been demonstrated in patients. This effect occurs in humans whenever there is adenosine released or whenever myocardial ischemia occurs. CSC may be used therapeutically in patients who suffer from ischemic damage due to stable angina, unstable angina or post-myocardial infarction angina to abrogate the effects of activation of the $A_{2a}$ receptor.

Several administration modalities may be utilized to treat patients with the $A_{2a}$ antagonists of the invention. These modalities are influenced by bioavailability factors. For example, if the compound is metabolized in the liver or excreted in the bile, some of the active compound absorbed from the gastrointestinal tract will be inactivated by the liver before it can reach the general circulation and be distributed to the site of action. It is not believed that the compounds of the invention will be subject to this first pass loss. Additionally, because the antagonists of the invention are polar and water soluble, it is expected that they will have a small volume of distribution, and thus be readily eliminated by the kidney. Moreover, binding of the antagonists to plasma proteins may limit their free concentrations in tissues and at their locus of action since it is only the unbound drug which equilibrates across membrane receptor sites.

Another factor affecting bioavailability is the distribution of the antagonists to tissues. Given the relatively small size of the compounds and their water solubility, it is anticipated that the compounds will have a relatively fast second phase of drug distribution. This distribution is determined by both the blood flow to the particular tissue of the organ such as the heart, as well as the rate at which the compounds diffuse into the interstitial compartment from the general circulation through the highly permeable capillary endothelium. Due to the relative hydrophilicity of some of the antagonists such as compound 24 and 1,3,7-trimethyl-8-[3-[[(3-carboxypropyl) carbonyl]amino]styryl]xanthine and 1,3,7-trimethyl-8-[3-[[ (4-carboxybutyl)carbonyl]amino]styryl]xanthine, it is anticipated that there will be no fat or other significant tissue reservoir of the antagonists which would contribute to third phase distribution-accumulation.

Patients may be perfused with the antagonists of the invention by dissolving them in normal saline solution or using emulsifying agents or cosolvents followed by intravenous administration every four to six hours. Effective doses usually range from 100 to 300 nM. For example, considering a 15 liter volume of distribution for a 70 kg patient, a loading dose ranging from 0.5 to 1.5 mg is preferably used. Depending on the half-life of CSC in the body, several doses, e.g., 1.5–4.5 mg may be administered per day.

Alternatively, a time-release or slow-release preparation may be utilized which allows for periodic or constant release of the antagonists over a given time period. This method would allow for a single dose of the antagonists in a given day. Methods for preparing such capsules are well known to those of skill in the art of drug delivery.

While the use of CSC as an $A_{2a}$ antagonist has been exemplified herein, other compounds have been identified which have high affinity for the $A_{2a}$ receptor and thus may also be used in the practice of the instant invention (39). These substituted 8-styryl derivatives of 1, 3, 7,-alkylxanthines were synthesized as potential $A_{2a}$-selective adenosine receptor antagonists. Following synthesis, potency was assessed at rat brain $A_1$ and $A_2$ receptors using radioligand binding assays. The starting stucture is shown below and substituted moieties listed in table I.

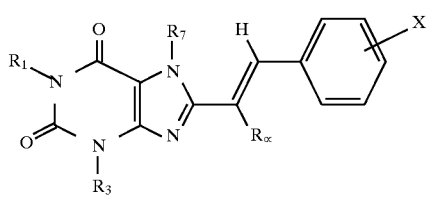

$R_1$, $R_3$ = methyl, ethyl, propyl, allyl
$R_7$ = H, methyl, alkyl ($C_2$–$C_8$)
$R_\alpha$ = H (unless noted)

Table I $A_{2a}$ receptor selectivity ratios of 8-styrylxanthine derivatives tested in radioligand binding assays at rat brain adenosine receptors.

TABLE I

Affinities of 8 Styrylxanthine Derivatives in Radioligand Binding Assays at Rat Brain $A_1$ and $A_2$-Receptors

| cmpd | $R_1.R_3$ | $R_7$ | X | $A_1/A_2$ ratio |
|---|---|---|---|---|
| 15b | Me | Me | H | 41 |
| 17b | Me | Me | 2-MeO | 18 |
| 19b | Me | Me | 3-MeO | 64 |
| 20b | Me | Me | 3-F$_3$ | 25 |
| 21b | Me | Me | 3-NO$_2$ | 11 |
| 22b | Me | Me | 3-NH$_2$ | 30 |
| 23 | Me | Me | 3-(AcNH) | 240 |
| 24 | Me | Me | 3-(HOOC(CH$_2$)$_2$CONH) | 250 |
| 25 | Me | Me | 3-(t-BOC-NH) | 30 |
| 26 | Me | Me | 3-[t-BOC)$_2$N] | 15 |
| 27b | Me | Me | 3-F | 190 |
| 28 | Me | Me | 3-Cl | 520 |
| 29b | Me | Me | 4-MeO | 44 |
| 32b | Me | Me | 3,4-(MeO)$_2$ | 70 |
| 33a | Me | H | 3,5-(MeO)$_2$ | 25 |
| 33b | Me | Me | 3,5-(MeO)$_2$ | >200 |
| 34b | Me | Me | 3,5-F$_2$ | 230 |
| 35 | Me | Me | 3,5-(MeO)$_2$-4-OH | 19 |
| 36 | Me | Me | 4-ACO-3,5-(MeO)$_2$ | 93 |
| 37 | Me | Me | 4-(PhCH$_2$O)-3,5-(MeO)$_2$ | 30 |
| 38 | Me | Me | 4-(4-NH$_2$-BuO)-3,5 (MeO)$_2$ | 36 |
| 39 | Me | Me | 4-[4-(tBOC-NH)BuO]-3,5-(MeO)$_2$ | 42 |
| 40 | Me | Me | 4-(4-NH$_2$-trans-CH$_2$CH=CHCH$_2$O-3,5-(MeO)$_2$ | 28 |
| 41 | Me | Me | 4-(4-AcNH-trans-CH$_2$CH=CHCH$_2$O)-3,5-(MeO)$_2$ | >50 |
| 42 | Me | Me | 4-(4-t-BOC-NH-trans-CH$_2$CH=CHCH$_2$O-3,5-(MeO)$_2$ | >40 |
| 43b | Me | Me | 2,3,4-(MeO)$_2$ | 34 |
| 44b | Me | Me | 3,4,5-(MO)$_3$ | 70 [>5600] |
| 45b | Et | Me | 3,4,5-(MeO)$_3$ | 34 |
| 46 | allyl | Me | 3,4,5-(MeO)$_3$ | 13 [>6700] |
| 51b | Pr | Me | 3-Cl | 14 |
| 52b | Pr | Me | 3,4-(MeO)$_2$ | 19 [190] |
| 53b | Pr | Me | 3,5-(MeO)$_2$ | 110 |

Other structures are suitable for use in the methods of the present invention. These compounds are set forth below:

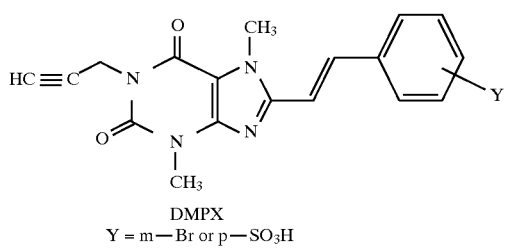

DMPX
Y = m—Br or p—SO$_3$H

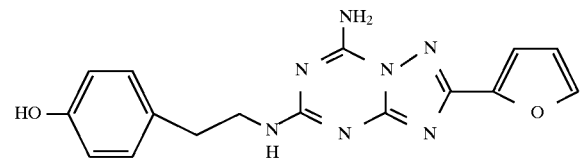

ZM241385

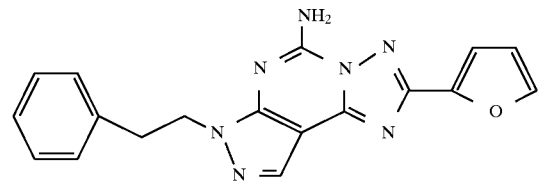

SCH58261

Brief ischemia, known as preconditioning ischemia, prior to a second sustained ischemia reduces the infarct size in the isolated perfused heart. Disclosed herein is a novel myocyte model of preconditioning using ventricular heart cells cultured from chick embryos. A brief hypoxic incubation of the cells was used to simulate preconditioning and a second sustained hypoxic exposure was able to induce injury. The protocol used to precondition the ventricular cells was similar to that employed to precondition the intact heart. The basic characteristics of preconditioning of the myocyte are similar to those of preconditioning of the intact heart (1–4, 11–13). Adenosine triggers as well as mediates the preconditioning effect on the myocytes, similar to its role in preconditioning of the intact heart. While the present study does not exclude a role for neuronal, vascular or blood cells in mediating preconditioning in the intact heart in vivo, the data provide conclusive evidence that inhibition of activation of certain adenosine receptors on ventricular cells can directly precondition the cells against injury.

A novel finding on the action of adenosine in myocyte preconditioning is that activation of the adenosine A2a receptor caused a decrease in the level of protection afforded by preconditioning hypoxia. In accordance with the present invention, blockade of the $A_{2a}$ receptor with the $A_{2a}$- selective antagonist CSC (27, 33) during preconditioning hypoxia enhanced the protection by preconditioning with a further decrease in the % cells killed and in the amount of CK released while stimulation with the $A_{2a}$-selective agonist CGS21680 had the opposite effect. Neither CSC nor CGS21680, when substituted for preconditioning hypoxia, had any protective or adverse effect on the extent of cell injury incurred during the ninety-minute hypoxia. Such results suggest that adenosine $A_{2a}$ receptor has primarily a modulatory role during preconditioning. Since activation of the $A_{2a}$ receptor resulted in an increase in calcium entry into the cardiac ventricular cell, the question arose regarding whether the increased calcium entry was the mechanism mediating the attenuation of preconditioning. Isoproterenol, acting via the β-adrenergic receptor-$G_s$-adenylyl cyclase pathway, forskolin, acting via the adenylyl cyclase, and BayK 8644, stimulating the L-type calcium channel directly, all caused a significant increase in the calcium entry. All three agents, when present during preconditioning hypoxia, attenuated the protection by preconditioning. The deleterious effect of all these agents on preconditioning was abolished by nifedipine and correlated with the nifedipine-mediated blockade of calcium entry. Neither isoproterenol, forskolin nor BayK8644 had any effect on the level of protection when cells were exposed to these agents for five minutes in place of the preconditioning hypoxia. Although the effect of these agents on the cytosolic calcium level is not known in the present study, the data support the notion that increased calcium entry during the initial brief hypoxia is the mechanism down-modulating the responsiveness of ventricular cells to preconditioning stimuli. Exposure of ventricular cells to nifedipine in the absence of preconditioning hypoxia did not simulate preconditioning, indicating that modulating the level of calcium entry alone could not induce preconditioning.

The possibility that some of these adenosine receptors may exert indirect effects via other contaminating cell types is unlikely. This is because the principal non-myocytes, the fibroblasts, express the $A_{2b}$ receptor and none of the $A_1$, $A_{2a}$ or $A_3$ agonists, at the concentrations used, could cause significant stimulation of the $A_{2b}$ receptor. The data show, for the first time, that a physiologic role of the adenosine $A_{2a}$ receptor is to mediate an antagonistic effect on the preconditioning of ventricular cells and that increased calcium entry during preconditioning stimuli is a novel mechanism capable of attenuating the responsiveness of heart cells to such stimuli. The novel pro- and anti-ischemic functions of the $A_{2a}$ and $A_3$ receptors, respectively, have implications for the treatment of ischemic heart disease. Receptor-selective adenosine analogs such as $A_{2a}$ receptor antagonists represent targets for new anti-ischemic pharmacologic agents.

REFERENCES

1. Murry, C. E., R. B. Jennings, and K. A. Reimer. 1986. Preconditioning with ischemia: A delay of lethal cell injury in ischemic myocardium. Circ. 74:1124–1136.
2. Downey, J. M. 1992. Ischemic preconditioning. Nature's own cardio protective intervention. Trends Cardiovasc. Med. 2:170–176.
3. Ely, S. W., R. M. Berne. 1992. Protective effects of adenosine in myocardial ischemia. Circulation 85:893–904.
4. Li, G. C., J. A. Vasquez, K. P. Gallagher, and B. R. Lucchesi. 1990. Myocardial protection with preconditioning. Circ. 82:609–619.
5. Deutsch, E., M. Berger, W. G. Kussmaul, J. W. Hirshfield, H. C. Hermann, W. K. Laskey. 1990. Adaptation to ischemia during percutaneous transluminal coronary angioplasty: Clinical, hemodynamic, and metabolic features. Circ. 82:2044–2051.
6. Cribier, A. L., R. Korsatz, Koning, P. Rath, H. Gamra, G. Stix, S. Merchant, C. Chan, B. Letac. 1992. Improved myocardial ischemic response and enhanced collateral circulation with long repetitive coronary occlusion during angioplasty: A prospective study. J. Am. Coll. Cardiol. 20:578–586.
7. Olafsson, B., M. B. Forman, D. W. Puett, A. Pou, C. U. Cates. 1987. Reduction of reperfusion injury in the canine preparation by intracoronary adenosine: Importance of the endothelium and the no-reflow phenomenon. Circ. 76:1135–1145.
8. Babbitt, D. G., R. Virmani, and M. B. Forman. 1989. Intracoronary adenosine administered after reperfusion limits vascular injury after prolonged ischemia in the canine model. Circ. 80:1388–1399.
9. Wyatt, D. A., S. W. Ely, R. D. Lasley, R. Walsh, R. Mainwaring, R. M. Berne, R. M. Mentzer. 1989. Purine-enriched asanguineous cardioplegia retards adenosine triphosphate degradation during ischemia and improves post ischemic ventricular function. J. Thorac. Cardiovasc. Surg. 97:771–778.
10. Miura, T., T. Ogawa, T. Iwamoto, K. Shimamoto, and O. Iimura. 1992. Dipyridamole potentiates the myocardial infarct size-limiting effect of ischemic preconditioning. Circ. 86:979–985.
11. Auchampach, J. A., G. J. Grover, and G. J. Gross. 1992. Blockade of ischemic preconditioning in dogs by the novel ATP dependent potassium channel antagonist sodium 5-hydroxydecanoate. Cardiovas. Res. 26:1054–1062.
12. Yao, Z., and G. J. Gross. 1994. A comparison of adenosine-induced cardioprotection and ischemic preconditioning in dogs. Efficacy, time course, and role of KATP channels. Circ. 89:1229–1236.
13. Schulz, R., J. Rose, G. Heusch. 1994. Involvement of activation of ATP-dependent potassium channels in ischemic preconditioning in swine. Am. J. Physiol. 267:H1341–H1352.
14. Tomai, F., F. Crea, A. Caspardone, F. Versaci, R. DePaulis, A. Penta de Peppo, L. Chiariello, P. A. Gioffre'. 1994. Ischemic preconditioning during coronary angioplasty is prevented by glibencladmide, a selective ATP-sensitive K+ channel blocker. Circulation 90:700–705.
15. Armstrong, S., C. E. Ganote. 1994. Adenosine receptor specificity in preconditioning of isolated rabbit cardiomyocytes: evidence of A3 receptor involvement. Cardiovasc. Res. 28:1049–1056.
16. Ikonomidis, J. S., L. C. Tumiati, R. D. Weisel, D. A. G. Mickle, R.-K. Li. 1994. Preconditioning human ventricular cardiomyocytes with brief periods of simulated ischemia. Cardiovasc. Res. 28:1285–1291.
17. Webster, K. A., D. J. Discher, N. H. Bishopric. 1995. Cardioprotection in an in vitro model of hypoxic preconditioning. J. Mol. Cell. Cardiol. 27:453–458.
18. DeHaan, R. L. 1967. Developmental changes in the calcium currents in embryonic chick ventricular myocytes. Dev. Biol. 16:216–249.
19. Galper, J. B., and T. W. Smith. 1978. Properties of muscarinic acetylcholine receptors in heart cell cultures. Proc. Natl. Acad. Sci. U.S.A. 75: 5831–5835.
20. Barry, W. H., and T. W. Smith. 1982. Mechanisms of transmembrane calcium movement in cultured chick embryo ventricular cells. J. Physiol. 325:243–260.
21. Marsh, J. D., D. Lachance, and D. Kim. 1985. Mechanism of b-adrenergic receptor regulation in cultured chick heart cells. Circ. Res. 57:171–181.

22. Liang, B. T., M. R. Hellmich, E. J. Neer, and J. B. Galper. 1986. Development of muscarinic cholinergic inhibition of adenylate cyclase in embryonic chick hearts: its relationship to changes in the inhibitory guanine nucleotide regulatory protein. J. Biol. Chem. 261:9011–9021.

23. Stimers, J. R., S. Liu, and M. J. Lieberman. 1991. Apparent affinity of the Na/K pump for ouabain in cultured chick cardiac myocytes. J. Gen. Physiol. 98:815–833.

24. Xu, H., J. Miller, and B. T. Liang. 1992. High-efficiency gene transfer into cardiac myocytes. Nucleic Acids Res. 20:6425–6426.

25. Liang, B. T. 1992. Adenosine Receptors and Cardiovascular Function. Trends in Cardiovascular Medicine 2:100–108.

26. Liang, B. T. 1989. Characterization of the adenosine receptor in cultured embryonic chick atrial myocytes: Coupling to modulation of contractility and adenylyl cyclase activity and identification by direct radioligand binding. J. Pharmacol. Exp. Ther. 249:775–784.

27. Liang, B. T., B. Haltiwanger. 1995. Adenosine A2a and A2b receptors in cultured fetal chick ventricular cells. High- and low-affinity coupling to stimulation of myocyte contractility and cyclic AMP accumulation. Circ. Res. 76:242–251.

28. Liang, B. T. and Morley, J. F.: A new Gs-mediated, cyclic AMP-independent stimulatory mechanism via adenosine A2a receptor in the intact cardiac cell. J Biol Chem, 271: 18678–18685, 1996.

29. Mestril, R., S.-H. Chi, M. R. Sayen, K. O'Reilly, W. H. Dillmann. 1994. Expression of inducible stress protein 70 in rat heart myogenic cells confers protection against simulated ischemia-induced injury. J. Clin. Invest. 93:759–767.

30. Hori, M., M. Inoue, M. Kitakaz, Y. Koretsune, K. Iwai, J. Tamai, H. Ito, A. Kitabatake, T. Sato, and T. Kamada. 1986. Role of adenosine in hyperemic response of coronary blood flow in microembolization. Am. J. Physiol. 250(Heart Circ. Physiol.19):H509–518.

31. Yamane, R., T. Nakamura, E. Matuura, H. Ishige, M. Fujimoto. 1991. A simple and sensitive radioimmunoassay for adenosine. J. Immunoassay 12:501–509.

32. Tietz, N. W. 1983. Fundamentals of Clinical Chemistry. Phila., W. B. Saunders Co.

33. Jacobson, K. A., O. Nikodijevic, W. L. Padgett, C. Gallo-Rodriguez, M. Maillard, and J. W. Daly. 1993. 8-(3-chlorostyryl)caffeine is a selective A2-adenosine antagonist in vitro and in vivo. Fed. Eur. Biochem. Soc. 323: 141–144.

34. Gallo-Rodriguez, C., X. Ji, N. Melman, B. D. Siegman, L. H. Sander, J. Orlina, B. Fischer, Q. Pu, M. E. Olah, P. J. M. Van Galen, G. L. Stiles, K. A. Jacobson. 1994. Structure-activity relationships of N6-benzyladenosine-5'-uronamides as A3-selective adenosine agonists. J. Med. Chem. 37:636–646.

35. Kim, H. O., X. Ji, S. M. Siddiqi, M. E. Olah, G. L. Stiles, K. A. Jacobson. 1994. 2-Substitution of N6-benzyladenosine-5'-uronamides enhances selectivity for A3 adenosine receptors. J. Med. Chem. 37:3614–3621.

36. Van Wylen, D. G. L. 1994. Effect of ischemic preconditioning on interstitial purine metabolite and lactate accumulation during myocardial ischemia. Circ. 89: 2283–2289.

37. Dobson, J. G. Jr. 1983. Mechanism of adenosine inhibition of catecholamine-induced responses in the heart. Circ Res. 52:151–160.

38. Liu, G. S., S. C. Richards, R. A. Olsson, K. Mullane, R. S. Walsh, J. M. Downey. 1994. Evidence that the adenosine A3 receptor may mediate the protection afforded by preconditioning in the isolated rabbit heart. Cardiovasc. Res. 28:1057–1061.

39. Jacobson, K. A., Gallo-Rodriguez, C., Melman, N., Fischer, B., Maillard, M., van Bergen, A., van Galen, P. J., Karton., Y. 1992. Structure-Activity Relationships of 8-Stryrylxanthines as A2-Selective Adenosine Antagonists. J. Med. Chem. 36:1333–1342.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for preventing or reducing ischemic damage to heart muscle cells in a patient in need of such treatment or at risk for said ischemic damage, comprising administering to said patient an antagonist to an A2a receptor in an amount effective to inhibit A2a receptor activation in the heart of said patient without activation of an A3 adenosine receptor.

2. A method as claimed in claim 1, wherein said antagonist is administered intravenously.

3. A method as claimed in claim 1, wherein said antagonist is administered by cardiac perfusion.

4. A method as claimed in claim 1, wherein said antagonist is administered orally.

5. A method as claimed in claim 1, wherein said antagonist is a compound selected from the group consisting of 1,3,7-trimethyl-8-styrylxanthine, 1,3,7-trimethyl-8-(2-methoxystyryl)xanthine, 1,3,7-trimethyl-8-(3-methoxystyryl)xanthine, 1,3,7-trimethyl-8-[3-(trifluoromethyl)styryl]xanthine, 1,3,7-trimethyl-8-(3-nitrostyryl)xanthine, 1,3,7-trimethyl-8-(3-aminostyryl)xanthine, 1,3,7-trimethyl-8-[3-(acetylamino)styryl]xanthine, 1,3,7-trimethyl-8-[3-[3(-carboxyl-1-oxopropyl)amino]-styryl]xanthine, 1,3,7-trimethyl-8-[3-[(tert-butyloxy)carbonyl]amino]-styryl]xanthine, 1,3,7-trimethyl-8-[3-[bis[(tert-butyloxy)carbonyl]amino]-styryl]xanthine, 1,3,7-trimethyl-8-(3-fluorostyryl)xanthine, 1,3,7-trimethyl-8-(4-methoxystyryl)xanthine, 1,3,7-trimethyl-8-(3,4-dimethoxystyryl)xanthine, 1,3-dimethyl-8-(3,5-dimethoxystyryl)xanthine, 1,3,7-trimethyl-8-(3,5-dimethoxystyryl)xanthine, 1,3,7-trimethyl-8-(3,5-difluorostyryl)xanthine, 1,3,7-trimethyl-8-[3,5-dimethoxy-4-(hydroxy)styryl]xanthine, 1,3,7-trimethyl-8-[3,5-dimethoxy-4-(acetoxy)styryl]xanthine, 1,3,7-trimethyl-8-[3,5-dimethoxy-4-(benzyloxy)styryl]xanthine, 1,3,7-trimethyl-8-[3,5-dimethoxy-4-[(4-aminobutyl)oxy]-styryl]xanthine, 1,3,7-trimethyl-8-[3,5-dimethoxy-4-[[4-[[(tertbutyloxy)-carbonyl]amino]butyl]oxy]styryl]xanthine, 1,3,7,-trimethyl-8-[3,5-dimethoxy-4-[(4-amino-trans-butenyl)oxy]styryl]xanthine, 1,3,7-trimethyl-8-[3,5-dimethoxy-4-[(4-acetylamino-trans-butenyl)oxy]styryl]xanthine, 1,3,7-trimethyl-8-[3,5-dimethoxy-4-[(4-t-butyloxycarbonylamino-trans-butenyl)oxy]styryl]xanthine, 1,3,7-trimethyl-8-(2,3,4-trimethoxystyryl)xanthine, 1,3,7-trimethyl-8-(3,4,5-trimethoxystyryl)xanthine, 7-Methyl-1,3-diethyl-8-(3,4,5-trimethoxystyryl)xanthine, 7-Methyl-1,3-diallyll-8-(3,4,5-trimethoxystyryl)xanthine, 1,3-dipropyl-7-methyl-8-(3-chlorostyryl)xanthine, 1,3-dipropyl-7-methyl-8-(3,4-dimethoxystyryl)xanthine, 1,3-dipropyl-7-methyl-8-(3,5-dimethoxystyryl)xanthine, DMPX, ZM241385, or SCH58261.

6. A method as claimed in claim 1, wherein said antagonist is 8-(3-chlorostyryl) caffeine.

7. A method as claimed in claim 1 wherein said antagonist is administered to said patient prior to a surgical procedure which may cause cardiac ischemic damage.

8. A method as claimed in claim 1, wherein said antagonist is administered to said patient during a surgical procedure which may cause cardiac ischemic damage.

9. A method as claimed in claim 1, wherein said antagonist is administered to said patient following a surgical procedure which may result in cardiac ischemic damage.

10. A method as claimed in claim 1, wherein said patient is in need of said treatment due to chronic stable angina.

11. A method as claimed in claim 1, wherein said patient is in need of said treatment due to unstable angina.

12. A method as claimed in claim 1, wherein said patient is in need of said treatment due to post-myocardial infarction angina.

13. A method for treating a patient to enhance myocardial responsiveness of heart muscle cells to preconditioning stimuli, comprising administering to a patient in need of said treatment, an A2a receptor antagonist in an amount effective to enhance myocardial response to said preconditioning stimuli, without activation of an A3 adenosine receptor.

14. A method as claimed in claim 13, wherein said patient is in need of said treatment due to chronic unstable angina.

15. A method as claimed in claim 13, wherein said patient is in need of said treatment due to stable angina.

16. A method as claimed in claim 13, wherein said patient is in need of said treatment due to post-myocardial infarction angina.

17. A method as claimed in claim 13 wherein said antagonist is administered to said patient prior to a surgical procedure which may cause cardiac ischemic damage.

18. A method as claimed in claim 13, wherein said antagonist is administered to said patient during a surgical procedure which may cause cardiac ischemic damage.

19. A method as claimed in claim 13, wherein said antagonist is administered to said patient following a surgical procedure which may result in cardiac ischemic damage.

20. A method as claimed in claim 13, wherein said A2a antagonist is a compound selected from the group consisting of 1,3,7-trimethyl-8-styrylxanthine, 1,3,7-trimethyl-8-(2-methoxystyryl)xanthine, 1,3,7-trimethyl-8-(3-methoxystyryl)xanthine, 1,3,7-trimethyl-8-[3-(trifluoromethyl)styryl]xanthine, 1,3,7-trimethyl-8-(3-nitrostyryl)xanthine, 1,3,7-trimethyl-8-(3-aminostyryl)xanthine, 1,3,7-trimethyl-8-[3-(acetylamino)styryl]xanthine, 1,3,7-trimethyl-8-[3-[3(-carboxyl-1-oxopropyl)amino]-styryl]xanthine, 1,3,7-trimethyl-8-[3-[(tert-butyloxy)carbonyl]amino]-styryl]xanthine, 1,3,7-trimethyl-8-[3-[bis[(tert-butyloxy)carbonyl]amino]-styryl]xanthine, 1,3,7-trimethyl-8-(3-fluorostyryl)xanthine, 1,3,7-trimethyl-8-(4-methoxystyryl)xanthine, 1,3,7-trimethyl-8-(3,4-dimethoxystyryl)xanthine, 1,3-dimethyl-8-(3,5-dimethoxystyryl)xanthine, 1,3,7-trimethyl-8-(3,5-dimethoxystyryl)xanthine, 1,3,7-trimethyl-8-(3,5-difluorostyryl)xanthine, 1,3,7-trimethyl-8-[3,5-dimethoxy-4-(hydroxy)styryl]xanthine, 1,3,7-trimethyl-8-[3,5-dimethoxy-4-(acetoxy)styryl]xanthine, 1,3,7-trimethyl-8-[3,5-dimethoxy-4-(benzyloxy)styryl]xanthine, 1,3,7-trimethyl-8-[3,5-dimethoxy-4-[(4-aminobutyl)oxy]-styryl]xanthine, 1,3,7-trimethyl-8-[3,5-dimethoxy-4-[[4-[[(tertbutyloxy)-carbonyl]amino]butyl]oxy]styryl]xanthine, 1,3,7,-trimethyl-8-[3,5-dimethoxy-4-[(4-amino-trans-butenyl)oxy]styryl]xanthine, 1,3,7-trimethyl-8-[3,5-dimethoxy-4-[(4-acetylamino-trans-butenyl)oxy]styryl]xanthine, 1,3,7-trimethyl-8-[3,5-dimethoxy-4-[(4-t-butyloxycarbonylamino-trans-butenyl)oxy]styryl]xanthine, 1,3,7-trimethyl-8-(2,3,4-trimethoxystyryl)xanthine, 1,3,7-trimethyl-8-(3,4,5-trimethoxystyryl)xanthine, 7-Methyl-1,3-diethyl-8-(3,4,5-trimethoxystyryl)xanthine, 7-Methyl-1,3-diallyll-8-(3,4,5-trimethoxystyryl)xanthine, 1,3-dipropyl-7-methyl-8-(3-chlorostyryl)xanthine, 1,3-dipropyl-7-methyl-8-(3,4-dimethoxystyryl)xanthine, 1,3-dipropyl-7-methyl-8-(3,5-dimethoxystyryl)xanthine, DMPX, ZM241385, or SCH58261.

\* \* \* \* \*